United States Patent [19]

Kessler

[11] Patent Number: 4,734,412

[45] Date of Patent: Mar. 29, 1988

[54] MEDICAMENT

[75] Inventor: Renate Kessler, Munich, Fed. Rep. of Germany

[73] Assignee: Peter M. Forrer Paliz, Basel, Switzerland

[21] Appl. No.: 693,431

[22] Filed: Jan. 22, 1985

[30] Foreign Application Priority Data

Jan. 25, 1984 [DE] Fed. Rep. of Germany ....... 3402507

[51] Int. Cl.$^4$ .................... A61U 31/55; A61U 31/495
[52] U.S. Cl. .................................. 514/221; 514/255
[58] Field of Search ............................... 514/255, 224

[56] References Cited

PUBLICATIONS

Chem. Abst. 96 (1982), 223282a1.
Merck Index, 9th Ed. (1976).
Chem. Abst., vol. 95 (1981), 571Y.

Primary Examiner—Stanley J. Friedman
Attorney, Agent, or Firm—Armstrong, Nikaido, Marmelstein & Kubovcik

[57] ABSTRACT

The invention concerns a medicament that contains a combination of cinnarizine and at least one benzodiazepine compound as active principle besides usual pharmaceutical adjuvants and/or carrier substances.

5 Claims, No Drawings

MEDICAMENT

The invention concerns a medicament containing a combination of cinnarizine with at least one benzodiazepine.

Benzodiazepines are used as ataractics and anxiolytics for the treatment of neurotic fundamental syndromes. They have a low toxicity.

Benzodiazepines are acting predominantly by accumulation of active metabolites in the central nervous system. This leads to a relatively long lasting therapeutic effect at relatively low doses. The differences in elimination time of the individual benzodiazepines determines their sedative or hypnotic properties. Typical representatives with sedative properties are chlordiazepoxide, diazepam, prazepam, oxazepam and bromazepam. Hypnotic properties are shown by nitrazepam, flurazepam and flunitrazepam. Clonazepam and diazepam have in addition antiepileptic properties.

Apart from the disturbed eqilibrium between the agitation processes and the inhibition of emotional reactions which leads on the one side to neuroses, on the other side to sleep disturbances, there exist still other important factors that will influence the sleep directly. Among these are disturbances of cerebral circulation, atherosclerotic alterations and vasoconstriction or restricted circulation in the cerebrum. All formations of the central nervous system are extremely sensitive to oxygen deficiency and they will in such case react with violent functional disorders.

Surprisingly it was found that the effect of benzodiazepines can be potentiated by concomitant doses of cinnarizine. Cinnarizine is used for example for cerebral circulation disorders. According to more recent findings the substance exerts also a calcium antagonistic action.

The synergistic, or respectively, potentiating effect of cinnarizine on benzodiazepines was determined by measuring the spontaneous motoricity in mice. Thereby the motoricity of the animals is counted by means of 19 photocells on the floor of the motility measuring device in the form of impulses. In order to eliminate accidental influences on the motility the tests were performed under rigidly controlled conditions consisting in: putting only 5 animals into each measuring device; performing all tests at the same time of the day in parallel under optimum and constant temperature conditions; taking animals all stemming from the same population and having been kept before the test start for 14 days in a joint cage, spending within this preparatory phase over 150 min daily in this motility measuring device for adaptation.

As typical representatives from the group of benzodiazepines which are usually classified according to substances with long, medium and short half life there were selected for the test diazepam (long half life), bromazepam (medium half life) and oxazepam (short half life). The oral $ED_{50}$ of these compounds were determined separately by the same method under identical criteria. The oral $ED_{50}$, determined grapically from the dose-effect curve, was 3.2 mg/kg for diazepam, 2.42 mg/kg for bromazepam and 1.55 mg/kg for oxazepam. The other benzodiazepines were tested with the same procedures.

The impulse count determined after 1 hour in the mesuring device was set as 100%. After that the animals of the control group received p.o. the vehicle (0.5% methyl cellulose solution with 2.5% Tween 20), the animals of the test group the test substance dissolved in the vehicle. The results are summarized in the table.

As the test results are showing the measured damping of the spontaneous motoricity by the benzodiazepine-cinnarizine combination is markedly stronger compared to the administration of the same benzodiazepine doses alone and its onset is distinctly earlier in time.

Cinnarizine exerts only a weak tranquillizing effect according to Eksp. Med. Morfol. 19 (1980), 212–216. The measured data after administration of cinnarizine alone are in the range of the control values and are indicating a slightly stimulating rather than a damping effect. This can be explained by the cerebral activity of this substance. Moreover no effect could be seen with cinnarizine in separate experiments for suppression of the behaviour—the real test for compounds with sedative activity—even in doses up to 300 mg/kg in mice.

The positive effect of cinnarizine on the tested benzodiazepines is measurable independently from their half life. The influence of the amount of cinnarizine is obviously divers; only in the case of the combination with oxazepam a longer lasting effect is shown with a higher cinnarizine dose. With the benzodiazepines of medium (bromazepam) and longer (diazepam) half life the higher dose of cinnarizine is causing a marked increase of motility towards the end of the test, as compared to the values with benzodiazepine alone.

From the results shown in the table it is revealed that the dose of the benzodiazepine can be reduced to achieve the same therapeutical effect by using a combination of a benzodiazepine with cinnarizine.

The medicaments according to the invention are administered per rectum in the form of rectal capsules or suppositories and per os in the form of tablets, dragees, hard or soft gelatine capsules using the usual pharmaceutical adjuvants as well as the usual carriers, disintegrants and lubricants.

The medicaments according to the invention are containing a benzodiazepine (I) and cinnarizine (II) at a weight ratio of I:II of 1:3 to 1:50, preferably 1:5 to 1:10. Suitably the medicament according to the invention contains 2 to 25 mg of the benzodiazepine component (I) and 10 to 75 mg cinnarizine per dose unit.

TABLE

Spontaneous motoricity after oral application in mice; mean percentage related to the corresponding group control value of 10 animals (2 tests of 5 animals each per group)

|  |  | mg/kg | 0 | 15 | 30 | 45 | 60 | 90 | 120 | 150 min per animal |
|---|---|---|---|---|---|---|---|---|---|---|
| Exp. 1 | control | — | 100 | 67.7 | 46.8 | 56.7 | 40.3 | 31.1 | 39.8 | — |
|  | cinnarizine | 20 | 100 | 70.5 | 50.1 | 52.3 | 44.6 | 46.7 | 52.4 | — |
|  |  | 100 | 100 | 68.4 | 49.6 | 51.1 | 48.2 | 42.3 | 49.3 | — |
|  | oxazepam | 1.55 | 100 | 53.3 | 78.9 | 21.4 | 14.1 | 30.7 | 12.4 | — |
| Exp. 2 | control | — | 100 | 54.5 | 41.6 | 50.8 | 34.5 | 50.2 | 56.8 | — |
|  | oxazepam + cinnarizine | 1.55 + 20.0 | 100 | 60.3 | 15.3 | 10.6 | 13.0 | 13.7 | 19.4 | — |

TABLE-continued

Spontaneous motoricity after oral application in mice; mean percentage related to the corresponding group control value of 10 animals (2 tests of 5 animals each per group)

|  |  | mg/kg | 0 | 15 | 30 | 45 | 60 | 90 | 120 | 150 min per animal |
|---|---|---|---|---|---|---|---|---|---|---|
| Exp. 3 | control | — | 100 | 59.5 | 51.2 | 43.8 | 38.2 | 68.0 | 68.5 | — |
|  | oxazepam | 1.55 | 100 | 38.8 | 12.3 | 13.6 | 8.4 | 32.3 | 9.5 | — |
|  | + cinnarizine | + 100.0 |  |  |  |  |  |  |  |  |
| Exp. 4 | bromazepam | 2.42 | 100 | 46.5 | 45.7 | 33.0 | 29.5 | 16.4 | 16.2 | 23.5 |
|  | bromazepam | 2.42 | 100 | 18.2 | 6.8 | 6.2 | 8.4 | 12.6 | 17.8 | 25.2 |
|  | + cinnarizine | + 20.0 |  |  |  |  |  |  |  |  |
|  | bromazepam | 2.44 | 100 | 20.6 | 7.2 | 6.1 | 10.8 | 14.5 | 20.6 | 44.5 |
|  | + cinnarizine | + 100.0 |  |  |  |  |  |  |  |  |
|  | control | — | 100 | 63.6 | 36.4 | 34.6 | 34.1 | 69.5 | 66.3 | 55.1 |
|  | diazepam | 3.2 | 100 | 39.4 | 41.7 | 29.9 | 26.6 | 10.5 | 15.6 | 19.8 |
|  | diazepam | 3.2 | 100 | 13.3 | 3.4 | 5.7 | 7.3 | 15.1 | 19.4 | 21.7 |
|  | + cinnarizine | + 20.0 |  |  |  |  |  |  |  |  |
|  | diazepam | 3.2 | 100 | 18.1 | 2.5 | 11.6 | 9.8 | 19.0 | 22.7 | 40.0 |
|  | + cinnarizine | + 150.0 |  |  |  |  |  |  |  |  |
| Exp. 5 | chlordiazepoxide | 3.4 | 100 | 42.5 | 43.3 | 34.8 | 33.5 | 14.4 | 16.6 | 20.4 |
|  | chlordiazepoxide | 3.4 | 100 | 15.6 | 6.4 | 5.8 | 6.6 | 16.8 | 17.2 | 23.3 |
|  | + cinnarizine | + 20.0 |  |  |  |  |  |  |  |  |
| Exp. 6 | prazepam | 3.05 | 100 | 44.0 | 36.5 | 32.2 | 28.6 | 13.2 | 12.5 | 18.6 |
|  | prazepam | 3.05 | 100 | 16.4 | 5.5 | 4.9 | 5.2 | 13.8 | 18.4 | 20.5 |
|  | + cinnarizine | + 20.0 |  |  |  |  |  |  |  |  |
| Exp. 7 | flurazepam | 2.65 | 100 | 47.4 | 40.8 | 35.2 | 26.5 | 21.2 | 22.4 | 24.6 |
|  | flurazepam | 2.65 | 100 | 20.6 | 8.4 | 6.8 | 7.8 | 9.6 | 12.8 | 20.5 |
|  | + cinnarizine | + 20.0 |  |  |  |  |  |  |  |  |
| Exp. 8 | clonazepam | 2.15 | 100 | 40.4 | 36.6 | 33.8 | 24.4 | 19.2 | 19.6 | 22.5 |
|  | clonazepam | 2.15 | 100 | 19.5 | 14.3 | 9.6 | 6.4 | 8.5 | 10.8 | 24.2 |
|  | + cinnarizine | + 20.0 |  |  |  |  |  |  |  |  |
| Exp. 9 | flunitrazepam | 1.94 | 100 | 42.5 | 34.2 | 29.8 | 26.5 | 22.4 | 22.6 | 26.5 |
|  | flunitrazepam | 1.94 | 100 | 16.4 | 9.5 | 6.6 | 7.2 | 10.8 | 16.5 | 23.2 |
|  | + cinnarizine | + 20.0 |  |  |  |  |  |  |  |  |
| Exp. 10 | nitrazepam | 1.80 | 100 | 44.6 | 42.4 | 39.6 | 24.5 | 19.6 | 18.4 | 19.8 |
|  | nitrazepam | 1.80 | 100 | 45.4 | 26.2 | 21.5 | 13.6 | 9.8 | 10.2 | 28.5 |
|  | + cinnarizine | + 20.0 |  |  |  |  |  |  |  |  |

EXAMPLES

1. Hard gelatine capsule

| | |
|---|---|
| Diazepam | 4.0 mg |
| Cinnarizine | 20.0 mg |
| Lactose D20 | 18.0 mg |
| Magnesium stearate | 0.8 mg |
| Talcum | 3.0 mg |
| Polyvinyl pyrrolidone | 2.5 mg |
| Corn starch | 7.2 mg |

2. Tablets

| | |
|---|---|
| Bromazepam | 5.0 mg |
| Cinnarizine | 50.0 mg |
| Hydroxypropyl cellulose | 5.0 mg |
| Microcrystalline cellulose | 33.0 mg |
| Gelatine | 2.8 mg |
| Stearic acid | 0.3 mg |
| Talcum | 2.0 mg |

3. Suppositories

| | |
|---|---|
| Chlordiazepoxide | 12.0 mg |
| Cinnarizine | 72.0 mg |
| Suppository mass H15 | 320.0 mg |
| Suppository mass W35 | 640.0 mg |

What we claim is:

1. A medicament, comprising besides usual pharmaceutical adjuvants and carrier substances, as the active principle, a combination of
   (a) at least one compound of the benzodiazepine group, and
   (b) cinnarizine in a weight ratio of from 1:3 to 1:50.

2. Medicament according to claim 1, characterized in that the benzodiazepine component is selected from at least one substance selected from the group consisting of: chlordiazepoxide, diazepam, prazepam, bromazepam, clonazepam, oxazepam, nitrazepam, flurazepam and flunitrazepam.

3. Medicament according to claim 1 or 2, characterized in that it contains the benzodiazepine and the cinnarizine in a weight ratio of from 1:5 to 1:10.

4. Medicament according to claim 3, characterized in that it is formulated for oral or rectal application.

5. Medicament according to claim 3, characterized in that it contains 2 to 25 mg of the benzodiazepine component per dose unit.

* * * * *